(12) United States Patent
Ranft

(10) Patent No.: US 11,207,252 B2
(45) Date of Patent: Dec. 28, 2021

(54) SYNERGISTIC PRESERVATIVE BLENDS

(71) Applicant: Lonza Ltd, Visp (CH)

(72) Inventor: Volker Ranft, Murg (DE)

(73) Assignee: Arxada AG, Lonzastrasse (CH)

( * ) Notice: Subject to any disclaimer, the term of this patent is extended or adjusted under 35 U.S.C. 154(b) by 0 days.

(21) Appl. No.: 14/898,810

(22) PCT Filed: Jun. 27, 2014

(86) PCT No.: PCT/EP2014/063649
§ 371 (c)(1),
(2) Date: Dec. 16, 2015

(87) PCT Pub. No.: WO2014/207179
PCT Pub. Date: Dec. 13, 2014

(65) Prior Publication Data
US 2016/0128920 A1    May 12, 2016

(30) Foreign Application Priority Data

Jun. 28, 2013  (EP) .................................... 13174309

(51) Int. Cl.
| A61K 8/36 | (2006.01) |
| A61Q 5/02 | (2006.01) |
| A61K 8/34 | (2006.01) |
| A61Q 19/10 | (2006.01) |

(52) U.S. Cl.
CPC ................ *A61K 8/36* (2013.01); *A61K 8/345* (2013.01); *A61Q 19/10* (2013.01); *A61K 2800/524* (2013.01); *A61Q 5/02* (2013.01)

(58) Field of Classification Search
None
See application file for complete search history.

(56) References Cited

U.S. PATENT DOCUMENTS

| 3,904,774 A * | 9/1975 | Dymsza ................. A23B 5/025 426/1 |
| 5,670,160 A * | 9/1997 | Eggensperger ........ A61K 8/498 252/380 |
| 6,447,793 B2 | 9/2002 | Aust et al. |
| 2008/0176957 A1 * | 7/2008 | Joerger ................... A61K 8/06 514/738 |
| 2008/0312195 A1 | 12/2008 | Simsch et al. |
| 2009/0035243 A1 | 2/2009 | Czamota et al. |
| 2009/0123577 A1 | 5/2009 | Beilfuss et al. |
| 2011/0086918 A1 * | 4/2011 | Ciccognani ............ A61K 8/345 514/557 |

FOREIGN PATENT DOCUMENTS

| DE | 1178771 B1 * | 3/2004 | ............... A61K 8/34 |
| EP | 1178771 | 3/2004 | |
| JP | H08-012535 | 1/1996 | |
| WO | WO 02/089759 | 11/2002 | |
| WO | WO 2011002929 A1 * | 1/2011 | ............. A01N 31/02 |
| WO | WO 2011/022345 | 2/2011 | |

OTHER PUBLICATIONS

ISR for PCT/EP2014/063649, dated Sep. 10, 2014.
Written Opinion for PCT/EP2014/063649.
EP 10810452.2 Search Report and Opinion, dated Sep. 6, 2013.
"Cosgard, conservant cosmetic agreat Ecocert—Mayam", 2005, Retrieved from the Internet: http://www.pcfarm.ro/produs/6748/Cosgard,-conservant-cosmetic-agreat—Ecocert—Mayam.
"Geosard ECT (was Mikrokill ECT)", 2010, Retrieved from the Internet: http://www.cosmeticingredients.co.uk/products.asp?prod=1209.
"Mikrokill® ECT", Arch Personal Care Products, L.P., Jan. 29, 2010, pp. 1-8, Retrieved from the Internet: http://az290931.vo.msecnd.net/web/www.in-cosmetics.com/_novadocuments/2198x$query$xvx$eq$x634484823552730000 or http://www.in-cosmetics.com/_novadocuments/4484.
Adina cosmetic ingredients, Nov. 2009 (Nov. 2009), Retrieved from the Internet: http://www.cosmeticingredients.co.uk/news_a.asp?story=67.
"Arch's Microkill ECI lives up to Cosmos and Ecocert expectations", Cosmetics International, Cosmetics Communications, London, GB, Dec. 11, 2009 (Dec. 11, 2009), p. 13, XP001526505, ISSN: 0963-6137.
"MSDS Mikrokill ECT", www.sinthaichem.com, Nov. 29, 2009, pp. 1-11, Retrieved from the Internet: http://www.sinthaichem.com/2011/attachments/download/99/Mikrokill%20ECT%20(139650)%20-%20MSDS.pdf.
Rosen et al., J. Soc. Cosmet. Chem., 24, 663-675, Sep. 16, 1973.

* cited by examiner

*Primary Examiner* — Dominic Lazaro
(74) *Attorney, Agent, or Firm* — Dority & Manning, P.A.

(57) ABSTRACT

A synergistic preservative composition comprises sorbic acid or a salt thereof, benzyl alcohol, and a mixture of (i) 1,2-propanediol and/or 1,3-propanediol, and (ii), 4-butanediol and/or 1,3-butanediol. The composition is particularly suited for the preservation of cosmetics and personal care products.

24 Claims, No Drawings

SYNERGISTIC PRESERVATIVE BLENDS

CROSS REFERENCE TO RELATED APPLICATIONS

This application is the U.S. National Stage entry of International Application Number PCT/EP2014/063649 filed under the Patent Cooperation Treaty and having a filing date of Jun. 27, 2014, which claims priority to European Patent Application No. 13174309.8 having a filing date of Jun. 28, 2013, all of which are hereby incorporated by reference herein in their entirety for all purposes.

The invention relates to synergistic preservative blends based on sorbic acid or salts thereof.

Sorbic acid is a naturally occurring acid that has been used for many years as a preservative for various products such as food- and feedingstuffs, pharmaceuticals and cosmetics. Sorbic acid is essentially non-toxic to humans and mammals and has only a faint odor which makes it attractive as a replacement for other preservatives having more problematic toxicological or sensorial properties. However, sorbic acid is a solid that is relatively sparingly soluble in water. For practical reasons, producers of liquid or semi-liquid cosmetics and personal care products such as shampoos, lotions, creams, liquid soaps etc. prefer liquid or easily soluble preservative formulations which can be easily admixed to their products. Moreover, the microbicidal potency of sorbic acids and its salts is not very high.

Therefore, it has been an object of the present invention to provide a sorbic acid-based preservative in liquid form that has an improved microbicidal activity.

According to the invention, this object has been achieved by the preservative blends of claim 1.

Surprisingly, it has been found that compositions comprising a butanediol selected from 1,4-butanediol and 1,3-butanediol, a propanediol selected from 1,2-propanediol and 1,3-propanediol, benzyl alcohol, and sorbic acid or a salt thereof are not only homogeneous liquids which can be easily admixed to cosmetic and personal care formulations, but have also a substantial synergistic effect as compared to the components taken alone.

According to the invention, the synergistic preservative compositions comprise
(a) from 1 to 20 wt. % of sorbic acid or a salt thereof;
(b) from 10 to 89 wt. % of benzyl alcohol; and
(c) from 10 to 89 wt. % of a mixture of
(i) 1,2-propanediol, 1,3-propanediol, or a mixture thereof; and
(ii) 1,4-butanediol, 1,3-butanediol, or a mixture thereof;
in a weight ratio of (i) to (ii) of 1:4 to 4:1;
based on the total weight of (a), (b) and (c).

In a preferred embodiment, the synergistic preservative compositions comprise
(a) from 1 to 10 wt. % of sorbic acid or a salt thereof;
(b) from 20 to 70 wt. % of benzyl alcohol; and
(c) from 20 to 70 wt. % of a mixture of
(i) 1,2-propanediol, 1,3-propanediol, or a mixture thereof; and
(ii) 1,4-butanediol, 1,3-butanediol, or a mixture thereof;
in a weight ratio of (i) to (ii) of 1:4 to 4:1;
based on the total weight of (a), (b) and (c).

More preferably, the synergistic preservative compositions comprise
(a) from 2 to 10 wt. % of sorbic acid or a salt thereof,
(b) from 20 to 50 wt. % of benzyl alcohol,
(c) from 40 to 70 wt. % of a mixture of
(i) 1,2-propanediol, 1,3-propanediol, or a mixture thereof; and
(ii) 1,4-butanediol, 1,3-butanediol, or a mixture thereof;
in a weight ratio of (i) to (ii) of 1:4 to 4:1;
based on the total weight of (a), (b) and (c).

Most preferably, the synergistic preservative compositions comprise
(a) from 4 to 10 wt. % of sorbic acid or a salt thereof,
(b) from 20 to 45 wt. % of benzyl alcohol,
(c) from 50 to 70 wt. % of a mixture of
(i) 1,2-propanediol, 1,3-propanediol, or a mixture thereof; and
(ii) 1,4-butanediol, 1,3-butanediol, or a mixture thereof;
in a weight ratio of (i) to (ii) of 1:4 to 4:1;
based on the total weight of (a), (b) and (c).

In one preferred embodiment, component (c) of the synergistic preservative composition is a mixture of (i) 1,2-propanediol and (ii) 1,4-butanediol.

More preferably, the synergistic preservative composition comprises
(a) from 4 to 10 wt. % of sorbic acid or a salt thereof,
(b) from 20 to 45 wt. % of benzyl alcohol,
(c) from 50 to 70 wt. % of a mixture of
(i) 1,2-propanediol; and
(ii) 1,4-butanediol;
in a weight ratio of (i) to (ii) of 1:4 to 2:1;
based on the total weight of (a), (b) and (c).

In another preferred embodiment, component (c) of the synergistic preservative composition is a mixture of (i) 1,3-propanediol and (ii) 1,3-butanediol.

More preferably, the synergistic preservative composition comprises
(a) from 4 to 10 wt. % of sorbic acid or a salt thereof,
(b) from 20 to 45 wt. % of benzyl alcohol,
(c) from 50 to 70 wt. % of a mixture of
(i) 1,3-propanediol; and
(ii) 1,3-butanediol;
in a weight ratio of (i) to (ii) of 1:4 to 2:1;
based on the total weight of (a), (b) and (c).

In addition to the main components (a), (b) and (c), the synergistic preservative compositions may contain auxiliaries such as solvents, anti-oxidants, stabilizers, colorants, fragrances and perfumes, or other additives known in the art.

The synergistic preservative compositions according to the invention are preferably used in a method for preventing or inhibiting microbial growth in cosmetics or personal care products (toiletries). The method comprises the step of adding to said products a preservative composition according to any one of the embodiments described above, in an amount of 0.1 to 10.0 wt. %, preferably 0.5 to 5.0 wt. %, calculated as sum of components (a), (b) and (c), and based on 100% total weight of the respective cosmetic or personal care product.

Suitable cosmetics and personal care products include, but are not limited to, shampoos, lotions, shower gels, bubble baths, bath oils, creams, baby products, liquid soaps, hair gels, make-up and sunscreens.

Preserved cosmetics and personal care products comprising a preservative composition according to any one of the embodiments described above, or obtained by the method described above, are also an object of the present invention.

The following non-limiting examples are intended to further illustrate the invention. Unless specified otherwise, all percentages are by weight (w/w).

EXAMPLE 1

Preparation of Preservative Concentrate

Sorbic acid (6 g) was dissolved under stirring in a mixture of benzyl alcohol (20 g), 1,2-propanediol (37 g) and 1,4-butanediol (37 g) until a clear colorless solution was obtained.

EXAMPLE 2

Challenge Tests, Bacteria

A) Reagents and Media

Tryptic soy broth: suspend 30 g of media (Merck) in 1 L of demineralized water. Dispense 9 mL into 20 mL glass tubes and autoclave (15 min @ 121° C.). Final pH is 7.3±0.2.

Tryptic soy agar plates: ready-to-use plates (Merck). Final pH is 7.3±0.2.

Sabouraud-2% glucose-agar plates: ready-to-use plates (Merck). Final pH is 5.6±0.2.

Sabouraud-2% glucose-agar slants: suspend 47 g of media (Merck) in 1 L of demineralized water. Dispense about 6 mL into 20 mL glass tubes and autoclave (15 min @ 121° C.). Final pH is 5.6±0.2. Slant tubes and allow them to cool.

NaCl-Peptone solution: dissolve 8.0 g of sodium chloride and 1.5 g of tryptone water in 1 L of demineralized water. Dispense 9 mL into 20 mL glass tubes and autoclave (15 min @ 121° C.).

Inactivation medium: for 1 L medium, dissolve 30.0 g of tryptic soy broth, 30.0 g of Tween® 80, 30.0 g of saponin, 1.0 g of histidine and 1.0 g of cystein in demineralized water. Divide into small aliquots and autoclave (15 min @ 121° C.).

B) Inoculum Preparation

A mixed inoculum containing approximately equal amounts of *Staphylococcus aureus* ATCC 6538, *Pseudomonas aeruginosa* ATCC 9027 and *Escherichia coli* ATCC 8739 was prepared according to the following procedure:

One colony of each bacteria strain was transferred from a stock culture to a tryptic soy agar plate which was incubated for 18-24 h at 37±2° C. Subsequently, some colonies of each of the thus-obtained cultures were transferred to a tryptic soy broth tube which was again incubated for 18-24 h at 37±2° C. to obtain a bacteria subculture, 200 µL of which were added to 2 mL of NaCl-peptone solution in a sterile plastic tube to obtain an inoculum containing approximately $10^9$ cfu/mL of the respective bacterium. Finally, the mixed inoculum was prepared by mixing equal volumes of each inoculum.

C) Challenge Test

The preservative composition obtained in Example 1 was added to in two different concentrations to 20 g samples of an unpreserved standard shampoo preparation for normal hair ("Shampoo ULD") supplied by McBride WCE, Estaimpuis, Belgium. For comparison purposes, additional 20 g samples were tested using equivalent amounts of each of the components of the preservative composition either alone or in two- or three-component combinations. Each sample was then inoculated with 200 µL of the mixed inoculum obtained in step A) and shaken vigorously to obtain a homogeneous contamination. The samples were then stored at room temperature and the bacteria count was determined in intervals of 7 days by taking 200 µL samples, mixing each of them with 1.8 mL of inactivation medium, and homogeneously plating 100 µL of the resulting mixtures on the surface of agar plates which were incubated for 2-3 days at 37±2° C. After the incubation period the colonies formed on the agar plates were counted and the results translated into cfu/mL. If necessary, serial dilutions in NaCl-peptone were prepared to cope with high bacteria counts. The results are compiled in Table 1 below. The entries at "0 days" reflect the starting level calculated from the bacteria count of the inoculum. Entries in italics indicate comparative tests.

TABLE 1

| Preservative/Concentration | Mixed Bacteria Germ Count (cfu/g) | | | | | | |
|---|---|---|---|---|---|---|---|
| | Inoculum | 0 days | 7 days | 14 days | 21 days | 28 days | pH |
| None/— | $4.3 \times 10^8$ | $4.3 \times 10^6$ | $>10^6$ | $>10^6$ | $>10^6$ | $>10^6$ | 5.7 |
| Example 1/1% [1] | $6.0 \times 10^8$ | $6.0 \times 10^6$ | $>10^3$ | <10 | <10 | <10 | 5.2 |
| Example 1/1.5% [2] | $6.0 \times 10^8$ | $6.0 \times 10^6$ | <10 | <10 | <10 | <10 | 5.1 |
| Sorbic Acid/0.06% | $5.9 \times 10^8$ | $5.9 \times 10^6$ | $>10^4$ | $>10^3$ | $6.7 \times 10^2$ | $2.0 \times 10^1$ | 5.4 |
| Sorbic Acid/0.09% | $5.9 \times 10^8$ | $5.9 \times 10^6$ | $2.0 \times 10^2$ | <10 | <10 | <10 | 5.4 |
| Benzyl Alcohol/0.3% | $3.2 \times 10^8$ | $3.2 \times 10^6$ | $4.3 \times 10^2$ | $>10^3$ | $>10^3$ | $>10^2$ | 5.4 |
| 1,4-Butanediol/0.56% | $4.1 \times 10^8$ | $4.1 \times 10^6$ | $>10^6$ | $>10^6$ | $>10^6$ | $>10^6$ | 4.9 |
| 1,2-Propanediol/0.56% | $4.1 \times 10^8$ | $4.1 \times 10^6$ | $>10^6$ | $>10^6$ | $>10^6$ | $>10^6$ | 4.7 |
| Sorbic Acid/0.06% + Benzyl Alcohol/0.2% | $5.9 \times 10^8$ | $5.9 \times 10^6$ | <10 | $3.0 \times 10^1$ | <10 | $1.3 \times 10^3$ | 5.2 |
| Sorbic Acid/0.09% + Benzyl Alcohol/0.3% | $5.9 \times 10^8$ | $5.9 \times 10^6$ | <10 | <10 | <10 | <10 | 5.2 |
| Sorbic Acid/0.06% + 1,2-Propanediol/0.37% + 1,4-Butanediol/0.37% | $5.9 \times 10^8$ | $5.9 \times 10^6$ | $>10^5$ | $4.8 \times 10^2$ | <10 | $1.7 \times 10^3$ | 5.3 |
| Benzyl Alcohol/0.2% + 1,2-Propanediol/0.37% + 1,4-Butanediol/0.37% | $5.9 \times 10^8$ | $5.9 \times 10^6$ | <10 | <10 | $1 \times 10^1$ | <10 | 5.7 |
| Sorbic Acid/0.09% + 1,2-Propanediol/0.56% + 1,4-Butanediol/0.56% | $5.9 \times 10^8$ | $5.9 \times 10^6$ | $>10^3$ | $8.9 \times 10^2$ | $1.8 \times 10^2$ | $>10^3$ | 5.2 |
| Benzyl Alcohol/0.3% + 1,2-Propanediol/0.56% + 1,4-Butanediol/0.56% | $5.9 \times 10^8$ | $5.9 \times 10^6$ | $4.0 \times 10^1$ | $1.0 \times 10^1$ | $1.0 \times 10^1$ | <10 | 5.7 |

[1] 1% of composition corresponding to 0.06% sorbic acid, 0.2% benzyl alcohol, 0.37% 1,2-propanediol, 0.37% 1,4-butanediol
[2] 1.5% of composition corresponding to 0.09% sorbic acid, 0.3% benzyl alcohol, 0.56% 1,2-propanediol, 0.56% 1,4-butanediol

EXAMPLE 3

Challenge Tests, Fungi

A) Inoculum Preparation

A mixed inoculum containing approximately equal amounts of *Candida albicans* ATCC 10231 and *Aspergillus niger* ATCC 16404 was prepared according to the following procedure:

One colony of *Candida albicans* was transferred from a stock culture to a Sabouraud-2% glucose-agar plate and incubated for 42-48 h at 30±2° C. Subsequently, a few colonies of the thus-obtained culture were transferred to about 2 mL of NaCl-peptone solution in a sterile plastic tube to obtain an inoculum with a microbial count of approximately $10^8$ cfu/mL.

About 100 μL of a stock solution of spores of *Aspergillus niger* were transferred to a Sabouraud-2% glucose-agar slant, spread uniformly over the surface and incubated for 10-12 days at 30±2° C. Subsequently, NaCl-Peptone solution (9 mL) was added to the culture slant together with some sterile glass beads and shaken vigorously. The resulting mixture was filtered through sterile glass wool into a sterile empty tube. The microbial count was checked by a plate count (2-5 days incubation at 30±2° C.) to ascertain that it was approximately $2 \times 10^7$ cfu/mL.

Finally, the mixed inoculum was prepared by mixing equal volumes of each inoculum.

The preservative composition obtained in Example 1 was added to an unpreserved shampoo preparation having a pH of 5.5 and the composition described in Table 2 below.

TABLE 2

| Ingredient | Supplier | INCI | wt.-% |
|---|---|---|---|
| Demin. Water | — | Aqua | 58.00 |
| Plantapon ® SF | BASF | Sodium Cocoamphoacetate, Glycerin, Lauryl Glucoside, Sodium Cocoyl Glutamate, Sodium Lauryl Glucose Carboxylate | 40.00 |
| Lamesoft ® PO65 | BASF | Aqua, Coco-Glucoside, Glyceryl Oleate | 1.00 |
| Citric Acid (40%) | Merck KGaA | Aqua, Citric Acid | 1.00 |

For comparison purposes, equivalent amounts of each of the components of the preservative composition were tested alone or in two-component combinations. The shampoo preparations were then inoculated with a mixture of the fungi and the germ count was determined in intervals of 7 days using essentially the same method as described in step C) of Example 2, with the exception that the plates were incubated for 3-5 days at 30±2° C. The results are compiled in Table 3 below. The entries at "0 days" reflect the starting level calculated from the bacteria count of the inoculum. Entries in italics indicate comparative tests.

TABLE 3

| Preservative/ Concentration | Mixed Fungi Germ Count (cfu/g) | | | | | | |
|---|---|---|---|---|---|---|---|
| | Inoculum | 0 days | 7 days | 14 days | 21 days | 28 days | pH |
| None/— | $5.7 \times 10^7$ | $5.7 \times 10^5$ | $>10^5$ | $>10^5$ | $>10^5$ | $>10^5$ | 5.4 |
| Example 1/1% [1)] | $9.7 \times 10^7$ | $9.7 \times 10^5$ | $>10^3$ | $>10^2$ | $1.7 \times 10^2$ | <10 | 5.4 |
| Example 1/1.5% [2)] | $9.7 \times 10^7$ | $9.7 \times 10^5$ | $>10^3$ | <10 | <10 | <10 | 5.4 |
| Sorbic Acid/0.06% | $4.4 \times 10^7$ | $4.4 \times 10^5$ | $>10^5$ | $>10^4$ | $>10^5$ | $>10^3$ | 5.4 |
| Sorbic Acid/0.09% | $4.4 \times 10^7$ | $4.4 \times 10^5$ | $>10^4$ | $>10^3$ | $>10^4$ | $1.5 \times 10^2$ | 5.4 |
| Benzyl Alcohol/0.3% | $5.7 \times 10^7$ | $5.7 \times 10^5$ | $>10^5$ | $>10^5$ | $>10^5$ | $>10^5$ | 5.4 |
| 1,4-Butanediol/0.56% | $3.2 \times 10^7$ | $3.2 \times 10^5$ | $>10^5$ | $>10^5$ | $>10^4$ | $>10^4$ | 4.9 |
| 1,2-Propanediol/0.56% | $3.2 \times 10^7$ | $3.2 \times 10^5$ | $>10^5$ | $>10^5$ | $>10^4$ | $>10^4$ | 4.7 |
| Sorbic Acid/0.09% + Benzyl Alcohol/0.3% | $4.4 \times 10^7$ | $4.4 \times 10^5$ | $<10^4$ | $>10^4$ | $>10^4$ | $5.2 \times 10^2$ | 5.4 |
| Sorbic Acid/0.09% + 1,2-Propanediol/0.56% + 1,4-Butanediol/0.56% | $4.4 \times 10^7$ | $4.4 \times 10^5$ | $<10^4$ | $>10^3$ | $>10^4$ | $5 \times 10^1$ | 5.4 |
| Benzyl Alcohol/0.3% + 1,2-Propanediol/0.56% + 1,4-Butanediol/0.56% | $4.4 \times 10^7$ | $4.4 \times 10^5$ | $>10^5$ | $>10^5$ | $>10^5$ | $>10^4$ | 5.4 |

[1)] 1% of composition corresponding to 0.06% sorbic acid, 0.2% benzyl alcohol, 0.37% 1,2-propanediol, 0.37% 1,4-butanediol
[2)] 1.5% of composition corresponding to 0.09% sorbic acid, 0.3% benzyl alcohol, 0.56% 1,2-propanediol, 0.56% 1,4-butanediol

EXAMPLE 4

Preparation of Preservative Concentrates

The procedure of Example 1 was repeated using different amounts of sorbic acid. Four compositions (A through D) were prepared. The concentrations of the ingredients of each composition are listed in Table 4 below.

TABLE 4

| Composition | Sorbic Acid | Benzyl Alcohol | 1,4-Butanediol | 1,2-Propanediol |
|---|---|---|---|---|
| A | 1.00% | 30.00% | 34.50% | 34.50% |
| B | 2.50% | 30.00% | 33.75% | 33.75% |
| C | 4.00% | 30.00% | 33.00% | 33.00% |
| D | 4.50% | 30.00% | 32.75% | 32.75% |

EXAMPLE 5

Challenge Tests

Two series of inocula (designated Challenge #1 and Challenge #2) were prepared according to the methods described in Examples 2 and 3, using the microorganisms *Staphylococcus aureus* ATCC 6538, *Pseudomonas aeruginosa* ATCC 9027, *Burkholderia cepacia* ATCC 25416,

*Klebsiella pneumoniae* ATCC 4352, *Enterobacter gergoviae* ATCC 33028 and *Candida albicans* ATCC 10231, and a "Mixed Molds" inoculum consisting of approximately equal amounts of *Aspergillus brasiliensis* ATCC 16404 and two *Penicillium* species isolated from cosmetic products. The inocula were added to samples of a test base (lotion) which had been preserved by addition of 2 wt.-% (based on the weight of the complete sample) of one of the preservative concentrates listed in Table 4, thus achieving sorbic acid concentrations of 0.02%, 0.05%, 0.08% and 0.09%, respectively, in the preserved samples. The composition of the test base is given below:

| Ingredient | INCI Name | wt.-% |
|---|---|---|
| Deionized Water | Aqua | 82.95 |
| Xanthan Gum | Xanthan Gum | 1.00 |
| Glycerol | Glycerin | 2.00 |
| Versene ® Na$_2$ | Disodium EDTA | 0.05 |
| Cetearyl Alcohol | Cetearyl Alcohol | 2.00 |
| Stearic Acid | Stearic Acid | 2.00 |
| Lonzest ™ MSA | Glyceryl Stearate & PEG 100 Stearate | 2.00 |
| Glycosperse ™ O-20 | Polysorbate 80 | 1.00 |
| pH Adjustment, Preservatives | — | 7.00 |

The amounts of inocula were chosen to achieve the numbers of colony forming units per gram of lotion listed in Table 5 below.

TABLE 5

| | Colony Forming Units Added per Gram of Product | |
|---|---|---|
| Organism | Challenge #1 | Challenge #2 |
| *S. aureus* | $3.6 \times 10^6$ | $3.2 \times 10^6$ |
| *P. aeruginosa* + *B. cepacia* | $3.2 \times 10^6$ | $2.5 \times 10^6$ |
| *K. pneumoniae* + *E. gergoviae* | $3.8 \times 10^6$ | $2.7 \times 10^6$ |
| *C. albicans* | $1.4 \times 10^5$ | $1.0 \times 10^5$ |
| Mixed Molds | $1.8 \times 10^5$ | $1.5 \times 10^5$ |

Samples (35 g each) were inoculated with approximately $2 \times 10^6$ bacteria per gram or $10^5$ yeast cells or mold spores per gram. Individual challenges were prepared from overnight slants of bacteria and yeast cultures and from heavily sporulating mold cultures, 7 to 10 days old. All samples were plated (bacteria in tryptic soy agar and fungi in malt agar) quantitatively for viable organisms after 24 hours and weekly for 4 weeks and the number of colony forming units per gram (cfu/g) of test base (lotion) was determined. Modified Letheen Broth with 0.5% Tween® 80 and 0.07% lecithin added was used as a neutralizer. Samples inoculated with mold spores were also plated after 48 hours. Four weeks after the initial challenge, samples were challenged again and the same sampling regime followed. For the control samples (without preservative) the cfu/g numbers were also determined at 0 h (i.e., immediately after the inoculation) after both Challenge #1 and Challenge #2. The results are compiled in Tables 6 to 11 below. The data in Table 11 relate to samples prepared with Composition D that had been aged before addition to the test base.

| Preservative (see Table 4) | Table No. |
|---|---|
| None (unpreserved control) | Table 6 |
| Composition A | Table 7 |
| Composition B | Table 8 |
| Composition C | Table 9 |
| Composition D | Table 10 |
| Composition D (aged*) | Table 11 |

*)After aging for 1 month at 50° C., followed by storage at room temperature for several months.

TABLE 6

| Test Organism | Challenge #1 | | | | | | |
|---|---|---|---|---|---|---|---|
| | 0 Hours | 24 Hours | 48 Hours | 7 Days | 14 Days | 21 Days | 28 Days |
| *S. aureus* | $1.0 \times 10^6$ | $1.5 \times 10^6$ | — | $5.8 \times 10^5$ | $1.6 \times 10^5$ | $4.4 \times 10^3$ | $<10^2$ |
| *P. aeruginosa* + *B. cepacia* | $1.1 \times 10^6$ | $2.9 \times 10^6$ | — | $>5.0 \times 10^7$ | $>5.0 \times 10^7$ | $>5.0 \times 10^7$ | $>5.0 \times 10^7$ |
| *K. pneumoniae* + *E. gergoviae* | $1.0 \times 10^6$ | $1.9 \times 10^6$ | — | $2.9 \times 10^7$ | $>5.0 \times 10^7$ | $>5.0 \times 10^7$ | $>5.0 \times 10^7$ |
| *C. albicans* | $5.2 \times 10^4$ | $1.4 \times 10^5$ | — | $2.2 \times 10^5$ | $4.0 \times 10^5$ | $3.6 \times 10^5$ | $2.5 \times 10^5$ |
| Mixed Molds | $1.0 \times 10^5$ | $1.2 \times 10^5$ | $9.0 \times 10^4$ | $4.0 \times 10^4$ | $2.8 \times 10^4$ | $4.0 \times 10^4$ | $2.1 \times 10^4$ |
| Test Organism | Challenge #2 | | | | | | |
| | 0 Hours | 24 Hours | 48 Hours | 7 Days | 14 Days | 21 Daysd | 28 Days |
| *S. aureus* | $1.8 \times 10^6$ | $1.5 \times 10^6$ | — | $1.3 \times 10^6$ | $1.7 \times 10^6$ | $1.1 \times 10^6$ | $2.0 \times 10^5$ |
| *P. aeruginosa* + *B. cepacia* | $>5.0 \times 10^7$ | $>5.0 \times 10^7$ | — | $>5.0 \times 10^7$ | $>5.0 \times 10^7$ | $>5.0 \times 10^7$ | $>5.0 \times 10^7$ |
| *K. pneumoniae* + *E. gergoviae* | $>5.0 \times 10^7$ | $>5.0 \times 10^7$ | — | $>5.0 \times 10^7$ | $>5.0 \times 10^7$ | $>5.0 \times 10^7$ | $>5.0 \times 10^7$ |
| *C. albicans* | $4.7 \times 10^5$ | $7.2 \times 10^5$ | — | $8.4 \times 10^5$ | $6.6 \times 10^5$ | $1.3 \times 10^6$ | $1.2 \times 10^6$ |
| Mixed Molds | $1.8 \times 10^5$ | $4.0 \times 10^4$ | $1.5 \times 10^5$ | $1.7 \times 10^5$ | $1.1 \times 10^5$ | $4.0 \times 10^4$ | $5.0 \times 10^4$ |

TABLE 7

| | Challenge #1 | | | | | |
|---|---|---|---|---|---|---|
| Test Organism | 24 Hours | 48 Hours | 7 Days | 14 Days | 21 Days | 28 Days |
| S. aureus | $1.1 \times 10^6$ | — | $7.9 \times 10^3$ | <10 | <10 | <10 |
| P. aeruginosa + B. cepacia | $7.2 \times 10^4$ | — | <10 | <10 | <10 | <10 |
| K. pneumoniae + E. gergoviae | $2.8 \times 10^5$ | — | <10 | <10 | <10 | <10 |
| C. albicans | $9.4 \times 10^4$ | — | $1.8 \times 10^4$ | $2.0 \times 10^2$ | <10 | <10 |
| Mixed Molds | $1.4 \times 10^4$ | $5.0 \times 10^3$ | $2.6 \times 10^3$ | $1.3 \times 10^3$ | $3.0 \times 10^2$ | $8.0 \times 10^1$ |

| | Challenge #2 | | | | | |
|---|---|---|---|---|---|---|
| Test Organism | 24 Hours | 48 Hours | 7 Days | 14 Days | 21 Days | 28 Days |
| S. aureus | $1.4 \times 10^6$ | — | $5.6 \times 10^4$ | $1.6 \times 10^2$ | <10 | <10 |
| P. aeruginosa + B. cepacia | $3.9 \times 10^4$ | — | <10 | <10 | <10 | <10 |
| K. pneumoniae + E. gergoviae | $4.1 \times 10^5$ | — | <10 | <10 | <10 | <10 |
| C. albicans | $7.2 \times 10^4$ | — | $3.7 \times 10^4$ | $1.7 \times 10^4$ | $1.6 \times 10^2$ | <10 |
| Mixed Molds | $6.0 \times 10^4$ | $3.0 \times 10^3$ | $6.0 \times 10^2$ | $1.6 \times 10^2$ | $1.7 \times 10^2$ | $1.4 \times 10^2$ |

TABLE 8

| | Challenge #1 | | | | | | Challenge #2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| S. aureus | $2.0 \times 10^5$ | — | <10 | <10 | <10 | <10 | $8.1 \times 10^5$ | — | $2.3 \times 10^2$ | <10 | <10 | <10 |
| P. aeruginosa + B. cepacia | $2.1 \times 10^2$ | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| C. albicans | $5.7 \times 10^4$ | — | $2.5 \times 10^3$ | <10 | <10 | <10 | $4.1 \times 10^4$ | — | $6.5 \times 10^4$ | $2.5 \times 10^2$ | <10 | <10 |
| Mixed Molds | $7.0 \times 10^3$ | $2.2 \times 10^2$ | $2.0 \times 10^1$ | <10 | <10 | <10 | $6.0 \times 10^4$ | $7.0 \times 10^2$ | <10 | <10 | <10 | <10 |

TABLE 9

| | Challenge #1 | | | | | | Challenge #2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| S. aureus | $5.0 \times 10^5$ | — | $9.0 \times 10^1$ | <10 | <10 | <10 | $1.2 \times 10^6$ | — | $2.2 \times 10^3$ | <10 | <10 | <10 |
| P. aeruginosa + B. cepacia | $7.1 \times 10^3$ | — | <10 | <10 | <10 | <10 | $3.8 \times 10^3$ | — | <10 | <10 | <10 | <10 |
| K. pneumoniae + E. gergoviae | $1.3 \times 10^3$ | — | <10 | <10 | <10 | <10 | <10 | — | <10 | <10 | <10 | <10 |
| C. albicans | $5.4 \times 10^4$ | — | $1.8 \times 10^3$ | <10 | <10 | <10 | $7.6 \times 10^4$ | — | $2.5 \times 10^3$ | <10 | <10 | <10 |
| Mixed Molds | $8.0 \times 10^3$ | $5.0 \times 10^2$ | $1.0 \times 10^1$ | <10 | <10 | <10 | $3.0 \times 10^4$ | $8.0 \times 10^2$ | <10 | <10 | <10 | <10 |

TABLE 10

| | Challenge #1 | | | | | | Challenge #2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| S. aureus | $2.4 \times 10^5$ | — | <10 | <10 | <10 | <10 | $1.1 \times 10^6$ | — | $2.6 \times 10^2$ | <10 | <10 | <10 |
| P. aeruginosa + B. cepacia | $1.6 \times 10^3$ | — | <10 | <10 | <10 | <10 | $7.2 \times 10^2$ | — | <10 | <10 | <10 | <10 |
| K. pneumoniae + E. gergoviae | $1.7 \times 10^2$ | — | <10 | <10 | <10 | <10 | $1.4 \times 10^3$ | — | <10 | <10 | <10 | <10 |
| C. albicans | $7.0 \times 10^4$ | — | $1.6 \times 10^2$ | <10 | <10 | <10 | $6.5 \times 10^4$ | — | <10 | <10 | <10 | <10 |
| Mixed Molds | $5.0 \times 10^3$ | $2.0 \times 10^4$ | <10 | <10 | <10 | <10 | $1.3 \times 10^4$ | $1.4 \times 10^4$ | <10 | <10 | <10 | <10 |

TABLE 11

| Test Organism | Challenge #1 | | | | | | Challenge #2 | | | | | |
|---|---|---|---|---|---|---|---|---|---|---|---|---|
| | 24 Hours | 48 Hours | 7 Days | 14 Days | 21 Days | 28 Days | 24 Hours | 48 Hours | 7 Days | 14 Days | 21 Days | 28 Days |
| S. aureus | $2.3 \times 10^5$ | — | <10 | <10 | <10 | <10 | $6.6 \times 10^5$ | — | <10 | <10 | <10 | <10 |
| P. aeruginosa + B. cepacia | $3.5 \times 10^3$ | — | <10 | <10 | <10 | <10 | $2.8 \times 10^3$ | — | <10 | <10 | <10 | <10 |
| K. pneumoniae + E. gergoviae | $9.2 \times 10^2$ | — | <10 | <10 | <10 | <10 | $3.4 \times 10^3$ | — | <10 | <10 | <10 | <10 |
| C. albicans | $8.2 \times 10^4$ | — | <10 | <10 | <10 | <10 | $7.3 \times 10^4$ | — | <10 | <10 | <10 | <10 |
| Mixed Molds | $1.4 \times 10^4$ | $5.0 \times 10^2$ | <10 | <10 | <10 | <10 | $1.9 \times 10^4$ | $1.2 \times 10^3$ | <10 | <10 | <10 | <10 |

The invention claimed is:

1. A preservative composition consisting essentially of
(a) from 1 to 6 wt. % of sorbic acid or a salt thereof;
(b) from 10 to 89 wt. % of benzyl alcohol;
(c) from 10 to 89 wt. % of a mixture of
 (i) 1,2-propanediol, 1,3-propanediol, or a mixture thereof; and
 (ii) 1,4-butanediol, 1,3-butanediol, or a mixture thereof
 in a weight ratio of (i) to (ii) of 1:4 to 4:1,
based on the total weight of (a), (b) and (c).

2. The preservative composition of claim 1, consisting essentially of
(a) from 1 to 4.5 wt. % of sorbic acid or a salt thereof,
(b) from 20 to 70 wt. % of benzyl alcohol,
(c) from 20 to 70 wt. % of a mixture of
 (i) 1,2-propanediol, 1,3-propanediol, or a mixture thereof; and
 (ii) 1,4-butanediol, 1,3-butanediol, or a mixture thereof,
 in a weight ratio of (i) to (ii) of 1:4 to 4:1,
based on the total weight of (a), (b) and (c).

3. The preservative composition of claim 2, wherein component (c) is a mixture of (i) 1,2-propanediol and (ii) 1,4-butanediol.

4. The preservative composition of claim 2, wherein component (c) is a mixture of (i) 1,3-propanediol and (ii) 1,3-butanediol.

5. The preservative composition of claim 1, wherein component (c) is a mixture of (i) 1,2-propanediol and (ii) 1,4-butanediol.

6. The preservative composition of claim 5, consisting essentially of
(a) from 1 to 6 wt. % of sorbic acid,
(b) from 20 to 45 wt. % of benzyl alcohol,
(c) from 50 to 70 wt. % of a mixture of
 (i) 1,2-propanediol; and
 (ii) 1,4-butanediol,
 in a weight ratio of (i) to (ii) of 1:4 to 2:1,
based on the total weight of (a), (b) and (c).

7. The preservative composition of claim 1, wherein component (c) is a mixture of (i) 1,3-propanediol and (ii) 1,3-butanediol.

8. The preservative composition of claim 7, consisting essentially of
(a) from 1 to 6 wt. % of sorbic acid,
(b) from 20 to 45 wt. % of benzyl alcohol,
(c) from 50 to 70 wt. % of a mixture of
 (i) 1,3-propanediol; and
 (ii) 1,3-butanediol,
 in a weight ratio of (i) to (ii) of 1:4 to 2:1,
based on the total weight of (a), (b) and (c).

9. The preservative composition of claim 1, consisting essentially of
(a) from 1 to 6 wt. % of sorbic acid or a salt thereof;
(b) from 10 to 89 wt. % of benzyl alcohol;
(c) from 10 to 89 wt. % of a mixture of
 (i) a propanediol consisting of 1,2-propanediol; and
 (ii) a butanediol comprising 1,4-butanediol, 1,3-butanediol, or a mixture thereof;
 in a weight ratio of (i) to (ii) of 1:4 to 4:1,
based on the total weight of (a), (b) and (c).

10. The preservative composition of claim 1, consisting essentially of
(a) from 2 to 6 wt. % of sorbic acid or a salt thereof;
(b) from 20 to 45 wt. % of benzyl alcohol;
(c) from 50 to 89 wt. % of a mixture of
 (i) 1,2-propanediol, 1,3-propanediol, or a mixture thereof; and
 (ii) 1,4-butanediol, 1,3-butanediol, or a mixture thereof
 in a weight ratio of (i) to (ii) of 1:4 to 2:1,
based on the total weight of (a), (b) and (c).

11. The preservative composition of claim 1, consisting essentially of
(a) from 1 to 6 wt. % of sorbic acid or a salt thereof;
(b) from 20 to 30 wt. % of benzyl alcohol;
(c) from 65 to 75 wt. % of a mixture of
 (i) 1,2-propanediol; and
 (ii) 1,4-butanediol;
 in a weight ratio of (i) to (ii) of 1:4 to 4:1,
based on the total weight of (a), (b) and (c).

12. The preservative composition of claim 1, wherein the composition exhibits a mixed fungi germ count of less than 10 cfu/g within 28 days during a challenge test wherein the mixed fungi contain Candida albicans and Aspergillus niger.

13. A preservative composition consisting of
(a) from 1 to 6 wt. % of sorbic acid or a salt thereof,
(b) from 10 to 89 wt. % of benzyl alcohol,
(c) from 10 to 89 wt. % of a mixture of
 (i) 1,2-propanediol, 1,3-propanediol, or a mixture thereof; and
 (ii) 1,4-butanediol, 1,3-butanediol, or a mixture thereof,
 in a weight ratio of (i) to (ii) of 1:4 to 4:1,
based on the total weight of (a), (b) and (c), and
(d) optionally one or more solvents, anti-oxidants, stabilizers, colorants, fragrances, and perfumes.

14. The preservative composition of claim 13, consisting of
(a) from 1 to 4.5 wt. % of sorbic acid or a salt thereof,
(b) from 20 to 45 wt. % of benzyl alcohol,
(c) from 50 to 70 wt. % of a mixture of
 (i) 1,2-propanediol, 1,3-propanediol, or a mixture thereof; and
 (ii) 1,4-butanediol, 1,3-butanediol, or a mixture thereof,
 in a weight ratio of (i) to (ii) of 1:4 to 2:1,
based on the total weight of (a), (b) and (c), and
(d) optionally one or more solvents, anti-oxidants, stabilizers, colorants, fragrances, and perfumes.

15. The preservative composition of claim 13, wherein component (c) is a mixture of (i) 1,2-propanediol and (ii) 1,4-butanediol.

16. The preservative composition of claim 13, wherein component (c) is a mixture of (i) 1,3-propanediol and (ii) 1,3-butanediol.

17. A method for inhibiting microbial growth in a cosmetic or personal care product, comprising the step of adding to said product a preservative composition according to claim 1 in an amount of 0.1 to 10.0 wt. %, calculated as sum of components (a), (b) and (c), and based on 100% total weight of said product.

18. The method of claim 17, wherein the preservative composition is added to the cosmetic or personal care product in an amount of 0.5 to 5.0 wt. %, calculated as sum of components (a), (b) and (c), and based on 100% total weight of said product.

19. The method of claim 17, wherein the cosmetic or personal care product is selected from the group consisting of shampoos, lotions, shower gels, bubble baths, bath oils, creams, baby products, liquid soaps, hair gels, make-up, and sunscreens.

20. A preserved cosmetic or personal care product obtained by the method of claim 17.

21. A method for inhibiting microbial growth in a cosmetic or personal care product, comprising the step of adding to said product a preservative composition according to claim 14 in an amount of 0.1 to 10.0 wt. %, calculated as sum of components (a), (b) and (c), and based on 100% total weight of said product.

22. The method of claim 21, wherein the preservative composition is added to the cosmetic or personal care product in an amount of 0.5 to 5.0 wt. %, calculated as sum of components (a), (b) and (c), and based on 100% total weight of said product.

23. The method of claim 21, wherein the cosmetic or personal care product is selected from the group consisting of shampoos, lotions, shower gels, bubble baths, bath oils, creams, baby products, liquid soaps, hair gels, make-up, and sunscreens.

24. A preserved cosmetic or personal care product obtained by the method of claim 21.

* * * * *